United States Patent
Tonson et al.

(10) Patent No.: US 9,897,571 B2
(45) Date of Patent: Feb. 20, 2018

(54) SIZE MARKER AND METHOD FOR CONTROLLING THE RESOLUTION OF AN ELECTROPHEROGRAM

(71) Applicant: MORPHO, Issy-les-Moulineaux (FR)

(72) Inventors: Benoit Tonson, Issy les Moulineaux (FR); Marcelin Ragot, Issy-les-Moulineaux (FR); Marina Pouet, Issy-les-Moulineaux (FR)

(73) Assignee: MORPHO, Issy les Moulineaux (FR)

( * ) Notice: Subject to any disclaimer, the term of this patent is extended or adjusted under 35 U.S.C. 154(b) by 250 days.

(21) Appl. No.: 14/731,291

(22) Filed: Jun. 4, 2015

(65) Prior Publication Data

US 2015/0355141 A1 Dec. 10, 2015

(51) Int. Cl.
G01N 27/447 (2006.01)

(52) U.S. Cl.
CPC ..... *G01N 27/44726* (2013.01); *G01N 27/447* (2013.01)

(58) Field of Classification Search
CPC ........... G01N 27/447; G01N 27/44717; G01N 27/44726; G01N 27/44791; C12N 15/101
See application file for complete search history.

(56) References Cited

U.S. PATENT DOCUMENTS

2005/0115837 A1    6/2005  Burgi et al.

FOREIGN PATENT DOCUMENTS

WO    WO 9314224    7/1993

OTHER PUBLICATIONS

Butler et al., "Locus-specific brackets for reliable typing of Y-chromosome short tandem repeat markers," Electrophoresis 2005, 26, 2583-2590.*
Yining Shi et al., DNA Sequencing and Multiplex STR Analysis on Plastic Microfluidic Devices, Electroporesis 2006 (9 pages).
Yining Shi et al., High-Resolution Single-Stranded DNA Analysis on 4.5 cm Plastic Electrophoretic Microchannels, Electrophoresis 2003 (7 pages).
John M. Butler, Application of Dual Internal Standards for Precise Sizing of Polymerase Chain Reaction Products Using Capillary Electrophoresis, Electrophoresis (1995) 16: 974-980.
John A. Luckey et al., Analysis of Resolution in DNA Sequencing by Capillary Gel Electrophoresis, J. Phys. Chem., 1993, 97(12), pp. 3067-3075.
Christoph Heller, Separation of Double-Stranded and Single-Stranded DNA in Polymer Solutions: II. Separation, Peak Width and Resolution, Electrophoresis, Jul. 1999; 20(10):198-86.
Eric Buel et al., Evaluation of Capillary Electrophoresis Performance Through Resolution Measurements, (J Forensic Sci. 2001; 46(2) :341-5).

* cited by examiner

*Primary Examiner* — Alexander Noguerola
(74) *Attorney, Agent, or Firm* — Blakely Sokoloff Taylor & Zafman LLP

(57) ABSTRACT

The invention concerns a size marker for electrophoresis, characterized in that it contains several pairs of molecules the sizes of which are selected to allow the generation of a succession of double-peaks in one same electropherogram, said double-peaks being spaced apart two by two by a distance greater than the distance separating the two peaks of a double-peak. The invention also concerns a method for controlling the resolution of an electropherogram produced with a said marker.

21 Claims, 17 Drawing Sheets

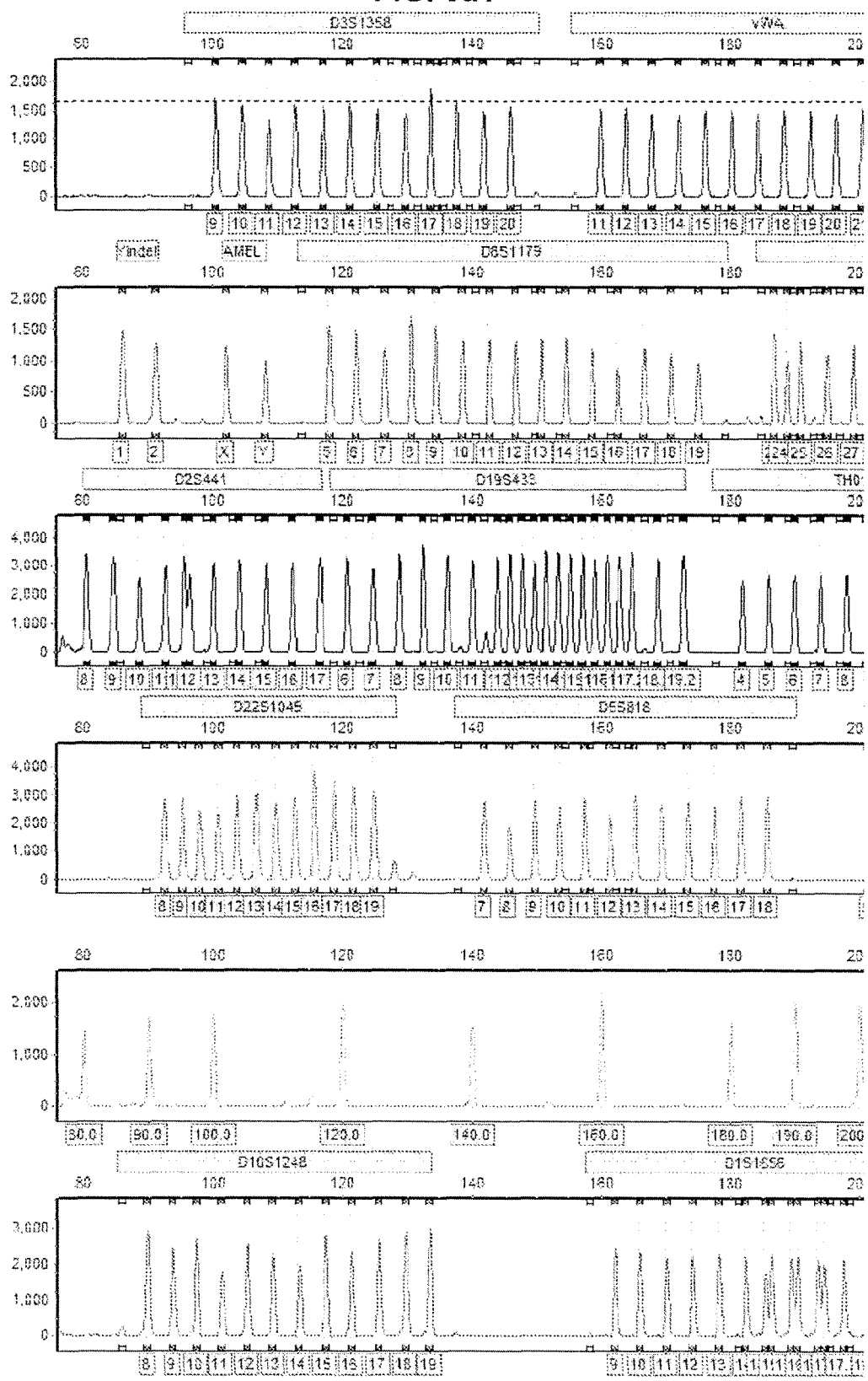
FIG. 3a1

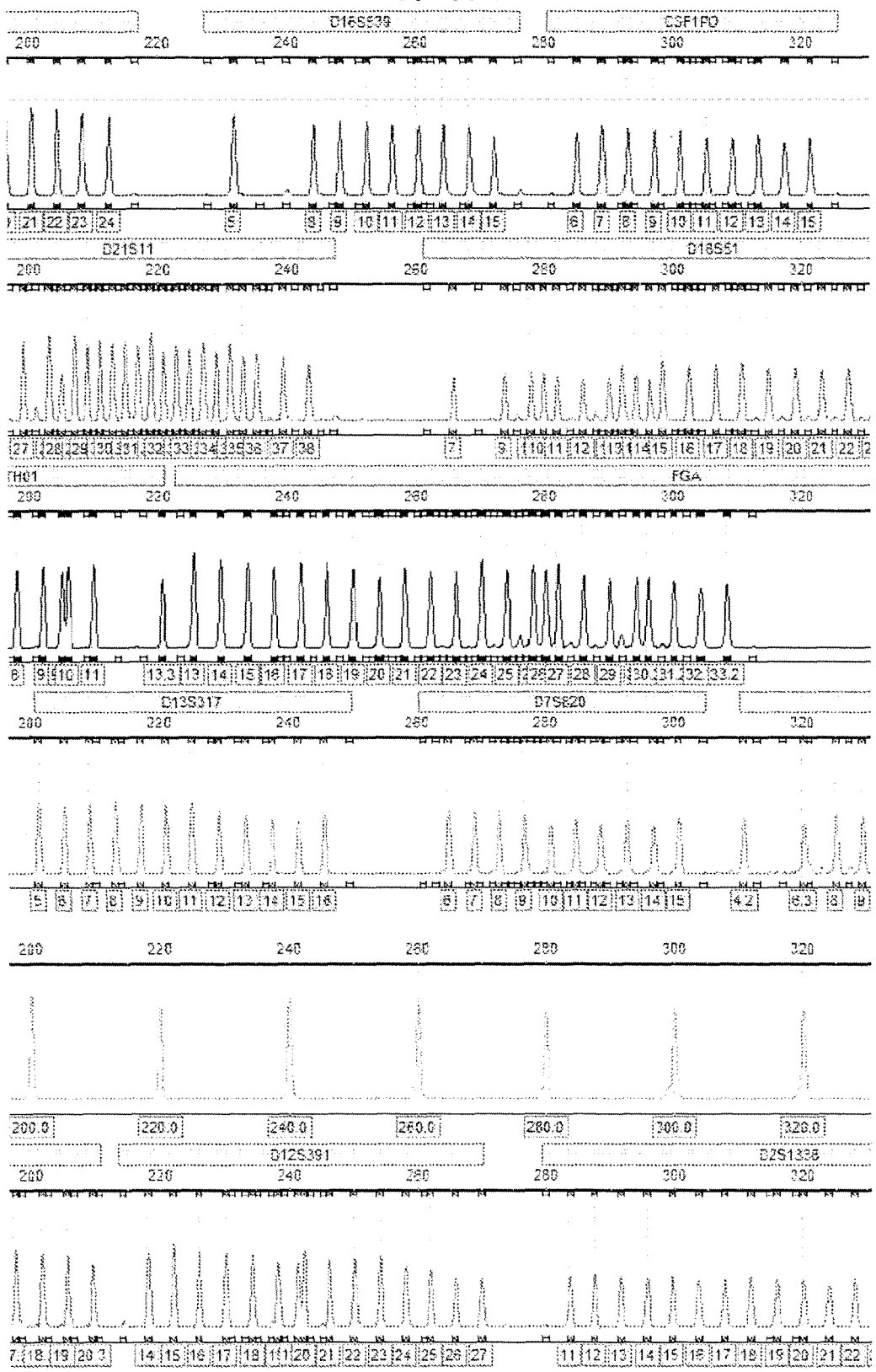
FIG. 3a2

FIG. 3a3
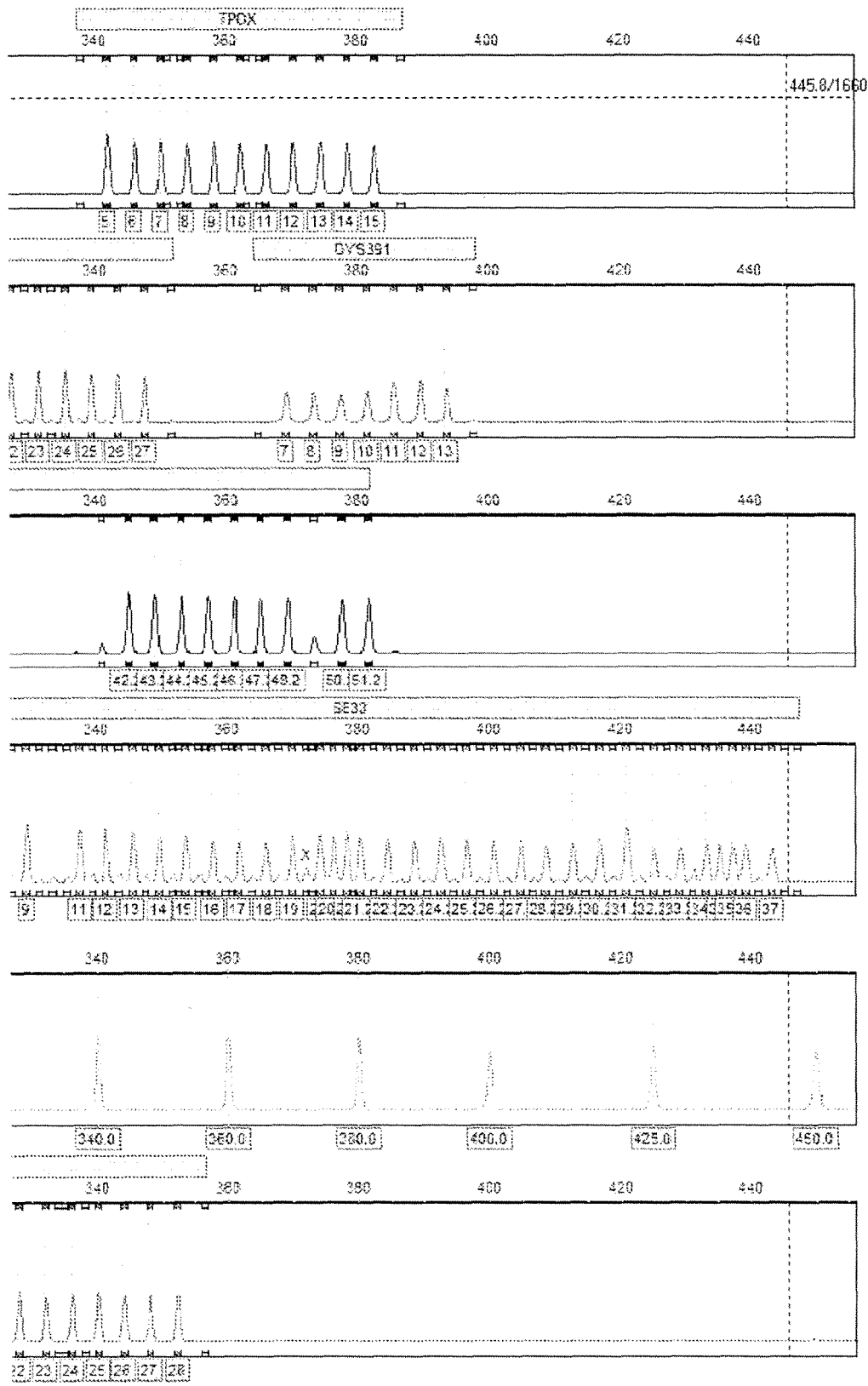

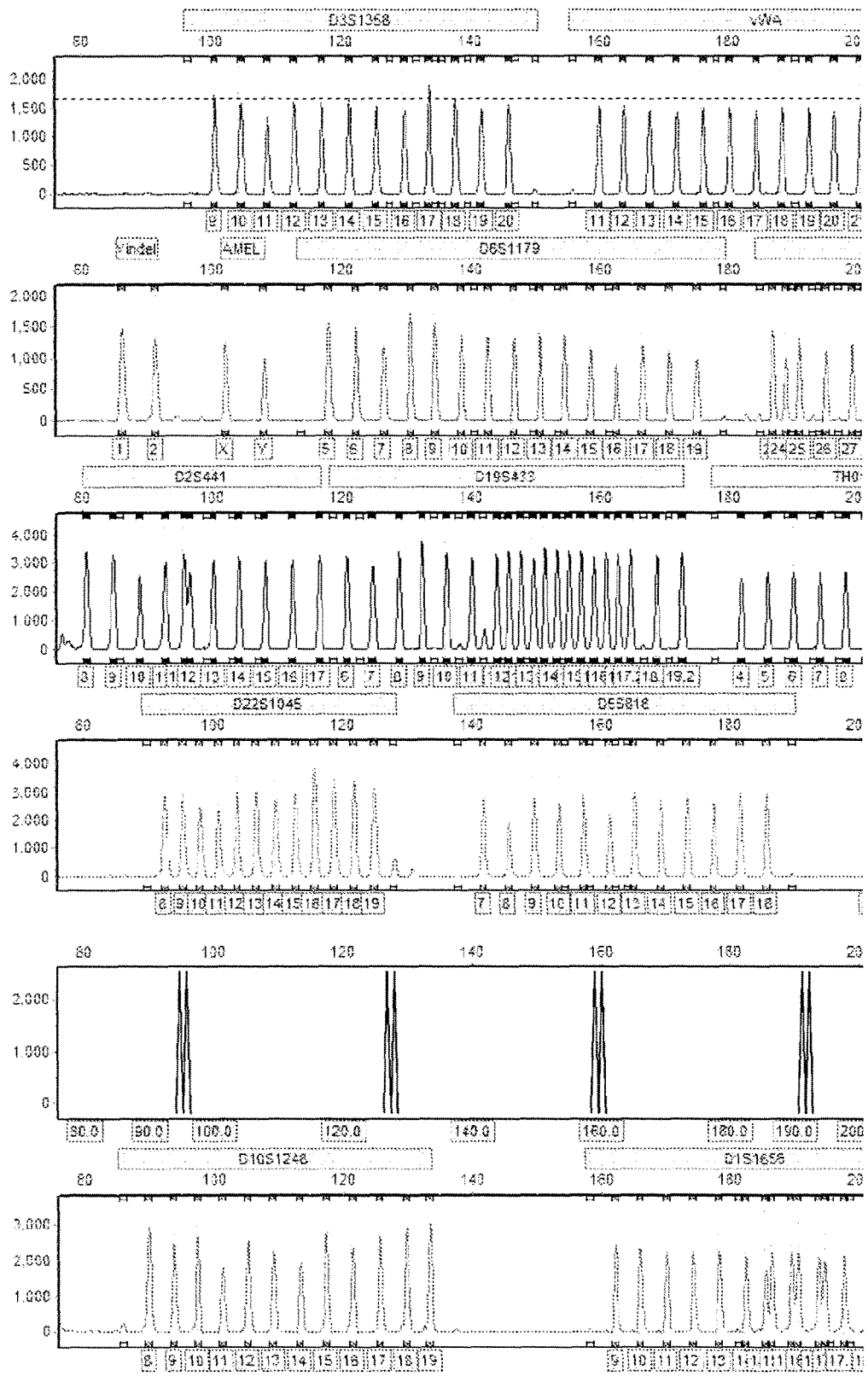
FIG. 3b1

FIG. 3b2
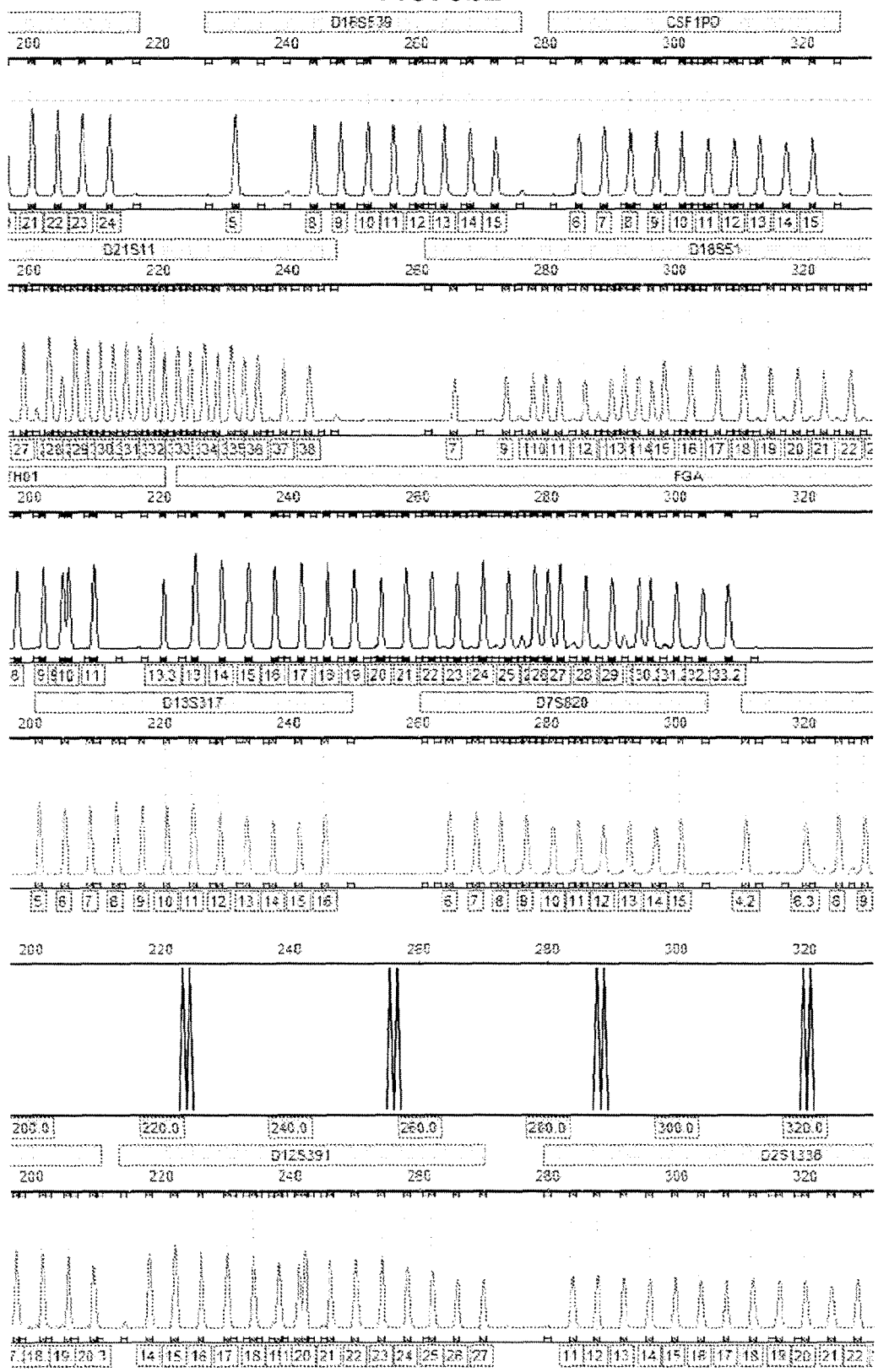

FIG. 3b3
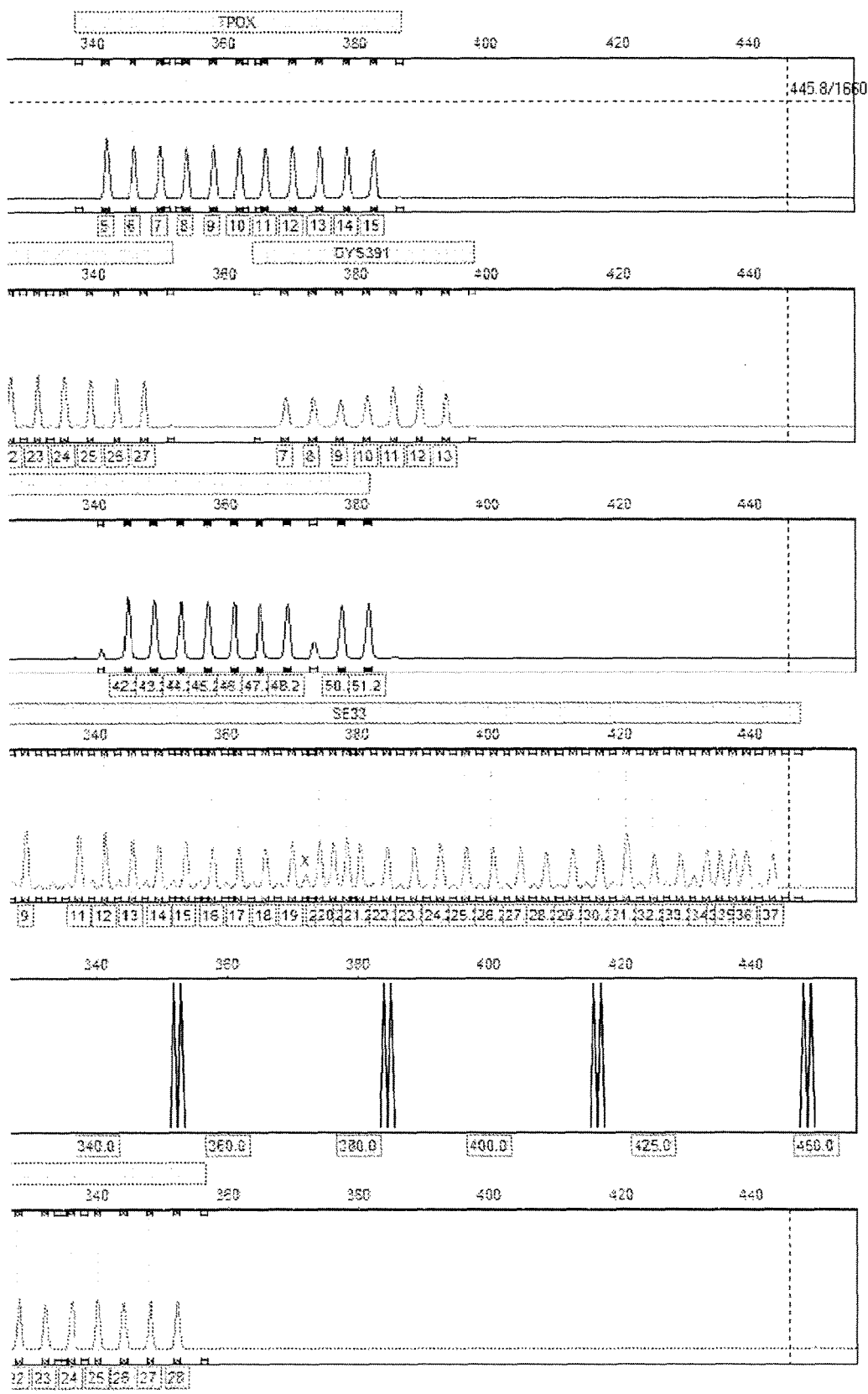

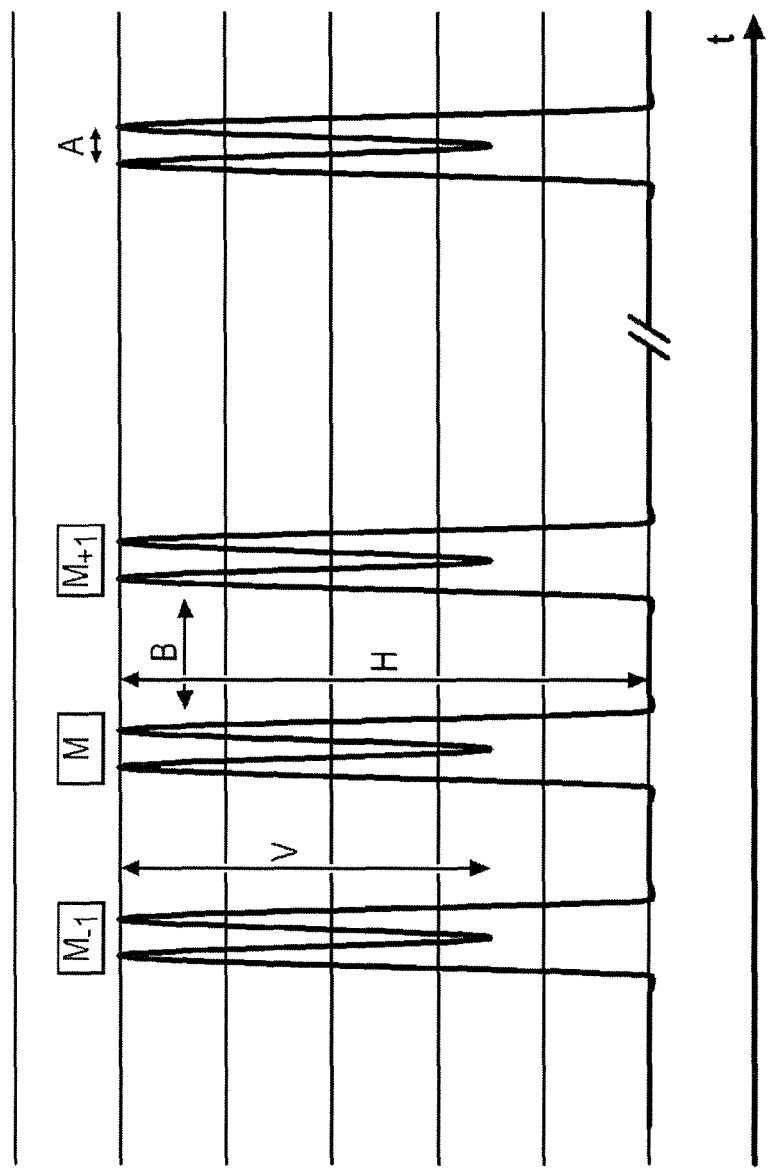

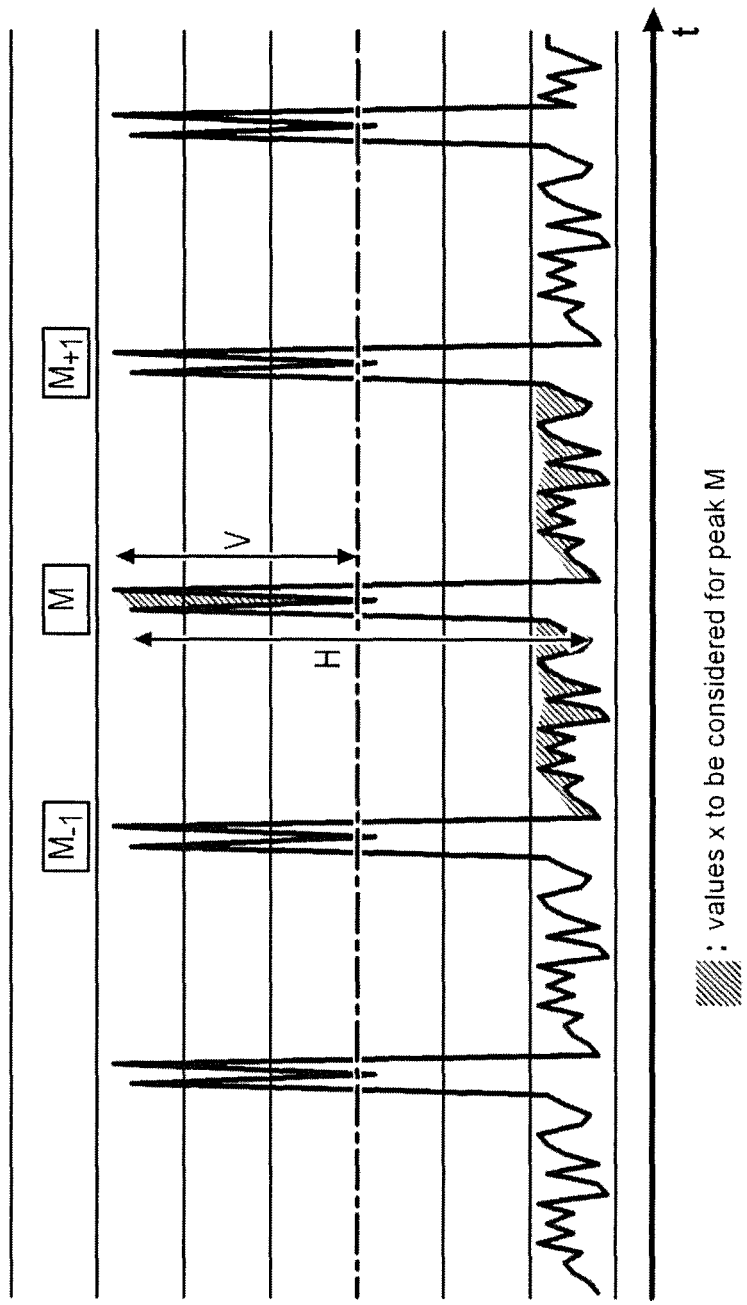

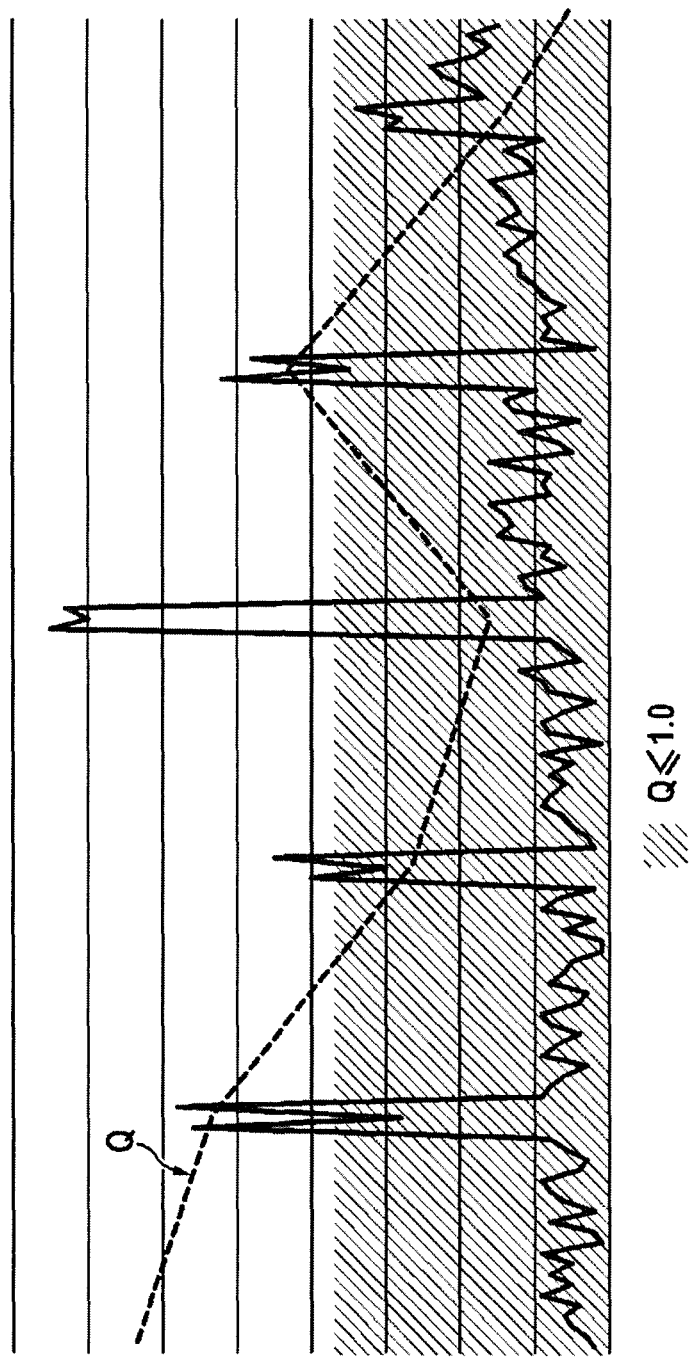

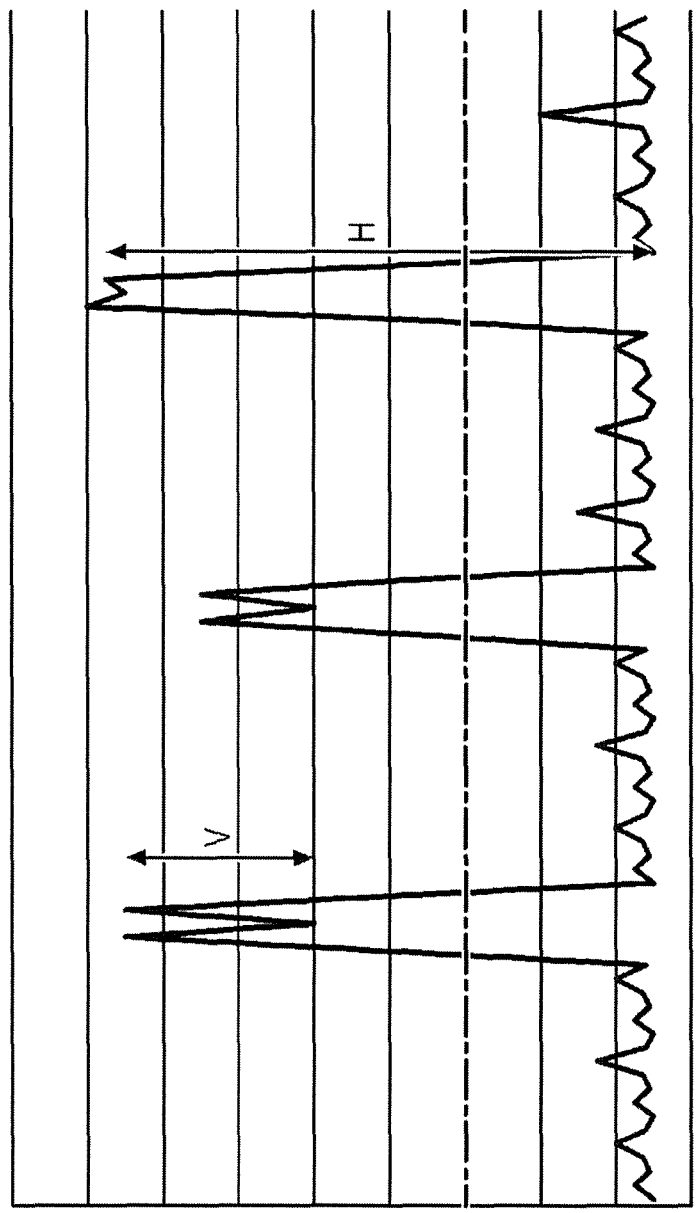

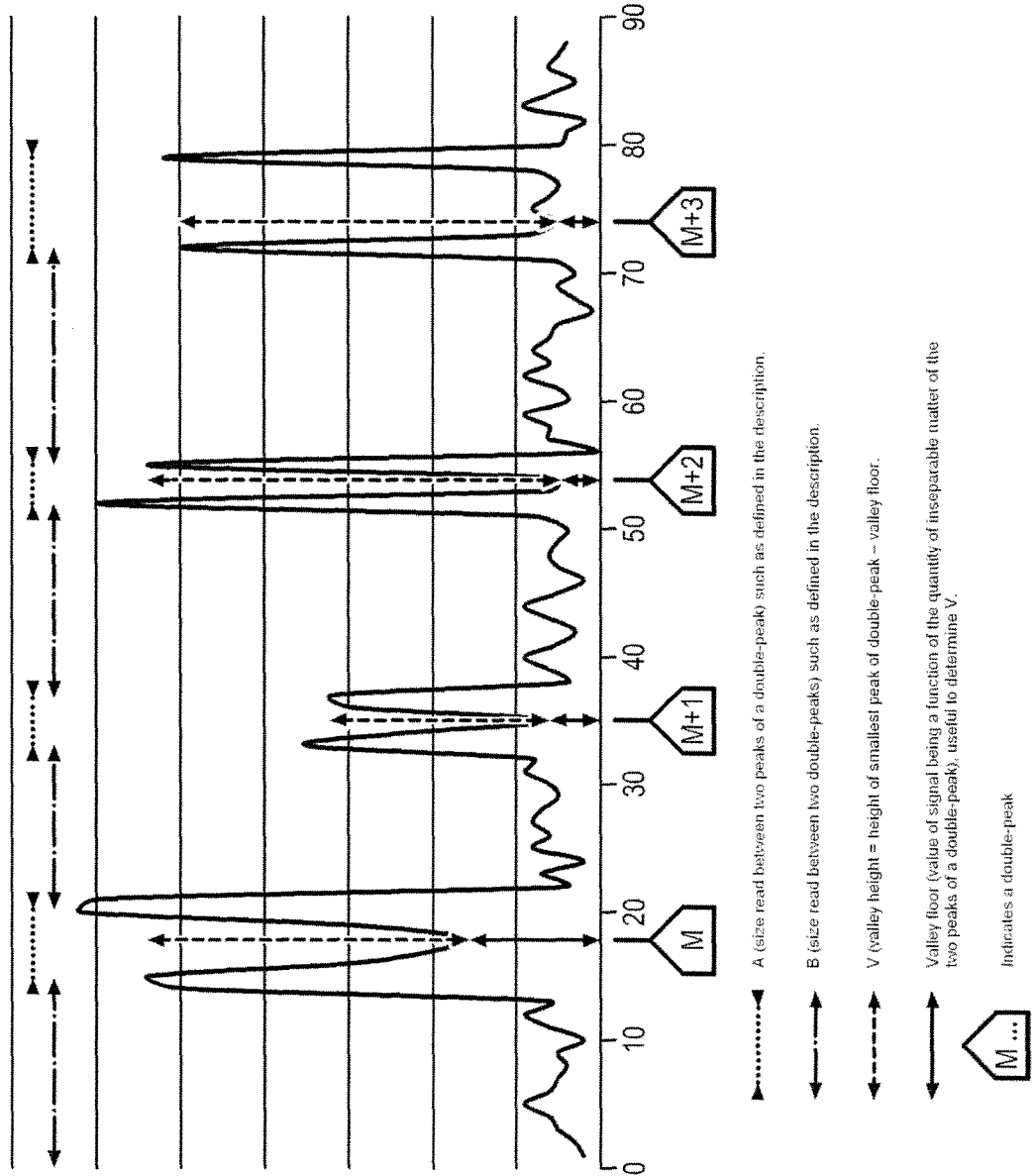

SIZE MARKER AND METHOD FOR CONTROLLING THE RESOLUTION OF AN ELECTROPHEROGRAM

The present invention concerns the controlling of the resolution of an electropherogram.

More specifically, the invention proposes a size marker allowing such control and a method to control an electropherogram obtained during electrophoresis analysis using a said marker.

Advantageously—but not limited thereto—it finds application in the field of capillary electrophoresis.

GENERAL TECHNICAL FIELD AND PRIOR ART

Electrophoresis—together with chromatography—is the main technique used in molecular biology for the separation and characterization of biochemical molecules. It is chiefly used for the separation of proteins or nucleic acids. In a given medium, the separation of particles is obtained in relation to their electrical charge, and for identical charges in relation to their size. Electrophoresis allows the separation of charged molecules after their migration in an (electric) force field.

Gel electrophoresis allows the separation of biological macromolecules (e.g. DNA) in a gel formed of a polymer matrix immersed in a conductive buffer, to which an electric field is applied. It acts as a sieve to separate the molecules as a function of size. Two main polymers are used: agarose and polyacrylamide. The concentration of polymer can be caused to vary relative to the concentration of buffer and the extent of its cross-linkage. The more the polymer is concentrated and cross-linked, the smaller the pore size of the gel. It is therefore possible to adjust the properties of the gel to the size of the molecules to be analysed.

Capillary electrophoresis was developed to separate chemical species inside a small capillary tube filled with a polymer and an electrolyte. It is currently considered to be a high-performance analytical separation method that is rapid, quantitative and reproducible. The interest in this new technology has significantly increased over the last twenty years, all the more so since its automation has allowed an improvement in the practicability of some electrophoretic separations that up until now were tedious to carry out. It has therefore become part of the instrumentation required by a modern analytical laboratory.

Capillary electrophoresis uses narrow capillaries (inner bore 10 to 200 µm) to obtain highly efficient electrophoretic separation of molecules varying greatly in size. The field of application of this technology is very vast and allows the analysis of complex macromolecules such as proteins and nucleic acids or solutes of small size such as organic medicinal products, inorganic anions and cations. Very high voltages (several tens of kV) are used to separate molecules on the basis of their different charge/size ratio. The instrumentation is relatively simple and comprises the following main elements: a high voltage generator, two buffer reservoirs and a capillary through which an optical detection system passes connected to a data acquisition module. The instrumentation assembly is computer-controlled.

Gel capillary electrophoresis is a particular capillary electrophoresis technique used when there are small differences in the electrophoretic mobility of the species to be separated. The gel contained in the capillaries sorts the molecules as per molecular weight which allows highly accurate determination of the molecular weights of polynucleotides and nucleic acid fragments. The gels used are generally formed of acrylamide-bisacrylamide copolymers. Their preparation requires treatment with a difunctional silane which polymerizes the monomers in situ inside the capillaries. The gels (or "matrixes") thus formed are grafted onto the wall and are capable of resisting electro-osmotic flows. Another possibility is to fill the capillaries with intermingled polymers. A large number of matrixes and capillaries of different type and size are currently commercially available. With this technique, molecules such as nucleic acids are separated on the basis of their different charge/size ratio. The size of nucleic acid molecules can be very accurately inferred from examination of the signals (or "peaks") which can be seen in the electropherogram.

Analyses of electropherograms can be performed automatically (for example using the systems: RaphidHIT™ 200, DNA Scan™ or Rapid DNA Analysis™ System) or in the laboratory using a genetic analyser (ABI Prism® Genetic Analyzer, MegaBACE sequencer).

For all the above reasons, gel capillary electrophoresis is currently widely used to obtain DNA profiles allowing the detection of allelic variations and hence differentiation between individuals (Butler, J. M., et al (1995) *Electrophoresis* 16: 974-980). When electrophoresis is used to detect allelic variations, the resolution of an electropherogram must allow the separation of nucleic acids having a size difference of only one base.

To control the reliability of the results obtained in an electropherogram, it is necessary to have available a method allowing exact evaluation of its resolution at every point thereof. The evaluation of this resolution provides essential information on the validity of the data obtained and the reliability of the method to obtain DNA profiles.

For automatic analyses, the resolution of the electropherogram is an indicator of the quality of analysis and of the equipment used (the drift of this parameter possibly being a sign that some elements must be changed). In other circumstances, in particular for conventional laboratory analyses, resolution can also be used to validate the relevance of the method used.

Several methods exist to evaluate resolution in an electropherogram (Luckey et al; *J. Phys. Chem.*, 1993, 97 (12), pp 3067-3075; Heller Cl. *Electrophoresis*. 1999 July; 20(10):1978-86). However no fully reliable method exists to obtain this resolution. The methods described in the above-cited publications are based on the signals measured in an electropherogram for each sample to be analysed. Yet these signals vary from one electropherogram to another which means that the value of resolution cannot be compared from one analysis to another and from one individual to another. More specifically, there is no guarantee that the resolution can be calculated (through lack of data) in reliable manner in a region in which this data is of interest. In addition, the data on which these methods are based are data allowing differentiation between individuals, and are not specific to calculation of resolution.

Also, the evaluation of the resolution of an electropherogram is always conducted a posteriori. In the event of doubt as to the validity of an electropherogram result, the analysis has to be entirely repeated.

Finally, the prior art methods allow the calculation of a global resolution value, which is unsuitable insofar as resolution is dependent on the number of bases and is therefore a local data value.

Therefore, up until the present time there has been no method which allows the reliable, objective monitoring, during analysis, of the resolution of an electropherogram.

General Presentation of the Invention

One general objective of the invention is to solve this issue and to propose a solution enabling the reliable and objective control of the resolution of all or part of an electropherogram.

A further objective of the invention is to propose a solution allowing the real-time or a posteriori monitoring of the evolution of the resolution of an electropherogram during an analysis.

Therefore according to a first aspect, the invention proposes a size marker containing pairs of molecules the sizes of which are selected to allow the generating in the electropherogram of a succession of double-peaks spaced two by two by a distance greater than the distance separating the two peaks of one same double-peak.

Unlike markers known in the prior art, which use isolated molecules of regularly distributed size (e.g. 100 bp, 150 bp, 200 bp, 250 bp, 300 bp, 350 bp, etc.), the proposed marker comprises several pairs of molecules of which the sizes are sufficiently close (e.g. [60, 61], [80, 81], [100, 101], and [120, 121] bp) to cause successive double-peaks to appear in an electropherogram.

By causing a said proposed marker to migrate at the same time as the analysed sample, it is possible, during an analysis, to control the sufficiency of the resolution of the electropherogram to cause these double-peaks to appear: if the double-peaks are sufficiently clearly apparent, this means that the resolution of the electropherogram in the region of the double-peaks is greater than the size difference between two molecules of one same pair.

The molecules of the marker may in particular be molecules of DNA (single or double strand), or molecules of RNA, polypeptides, proteins, organic medicinal products, inorganic anions and cations, etc.

In particular the double-peaks can be obtained using a mixture of several pairs of DNA molecules, the size of the DNA molecules within each pair differing by a base pair. Two DNA molecules the size of which only differs by one base pair (i.e. two DNA molecules containing x base pairs and x+1 base pairs respectively) generate two very close peaks in an electropherogram that are separated by a "valley" (a said pattern is hereafter called a "double-peak"). In this precise case, so that the resolution in a region of the electropherogram is smaller than one base, it is sufficient that the difference in height between the lower of the two peaks and the hollow between two peaks should be able to be differentiated from noise.

By "valley" in the present invention is meant the region of the electropherogram separating the two maxima of a double-peak. The height V of a valley is equal to the height of the least high peak of its double-peak, less the height of the valley floor (cf. FIG. 8).

The height of the valley floor is determined for example as being:

- the height of the minimum point of the valley when there exists a single point of slope change between the two peaks (minimum point where the slope of the electropherogram changes from negative to positive between the two peaks);
- or, when there are several points of slope change between the two peaks, the maximum height of the electropherogram between the points of slope change where the slope of the electropherogram changes from negative to positive.

The proposed size marker advantageously comprises at least three pairs of molecules to generate a succession of double-peaks in an electropherogram.

The molecules contained in this marker are a function i) of the type of compounds of interest to be analysed, ii) their size, iii) the electrophoresis system used and iv) of the desired resolution around the expected peak for the compound of interest.

In addition, the size difference ("b") between the pairs of molecules contained in said marker and which correspond to successive double-peaks is twice greater than the size difference ("a") between two molecules of one same pair (b>2a).

In one preferred embodiment, the size difference ("a") between two molecules of one same pair is between 1 and 6 size units.

In another preferred embodiment, these molecules are single strand DNA and the size difference ("a") between two molecules of one same pair is equal to one base pair, whilst "b" is equal to between 20 and 60 base pairs, preferably it is equal to 32 base pairs.

According to a further aspect of the invention, there is proposed a method for controlling the resolution of an electropherogram, characterized in that a signal is processed corresponding to said electropherogram and/or data corresponding thereto to detect the presence of the double-peaks corresponding to the pairs of molecules of a marker as claimed.

In one possible embodiment, to detect the presence of a double-peak, comparative processing is performed whereby the ratio between the following is compared with a threshold:

- the difference in height between the smallest peak of a double-peak and the valley of this double-peak; and
- three times the value of the standard deviation ($\sigma$) of the height of the valleys extending from the preceding double-peak to the following double-peak.

In particular, the curve of this ratio can be presented superimposed over an electropherogram corresponding thereto.

As a variant, to detect the presence of a double-peak, the slope changes of the electropherogram signal are detected and it is detected that its slope becomes negative after a first maximum, passes through zero and then re-becomes positive to reach a second maximum.

As a further embodiment to detect the presence of a double-peak, comparative processing is performed whereby the comparison is made between a threshold and the ratio between the height of the valley between two peaks and the height of the smaller of the two peaks.

The proposed solution has numerous advantages.

In particular, throughout the analysis of a sample, it allows controlling the resolution of an electropherogram at every point thereof, in order to detect as early as possible whether the analysis is usable or whether some elements in the system must be changed. In other words, during the electrophoresis phase it allows verification of the resolution of the analysis region in progress (and optionally to exclude portions of the electropherogram in which resolution is insufficient, or to stop analysis in the event of diverging resolution). In addition, it allows verification of any drift of resolution over time to control the obsolescence/fatigue/validity of the machine and of the capillary.

By means of this method, skilled persons are therefore easily able to verify the reliability of a region of an electropherogram via its local resolution including during the processing of data. For example they are quickly able to determine whether the resolution obtained is compatible with the requirements of the detection of allelic variations (detection of difference by one base pair).

In addition, the proposed solution has generic application:

it can be used to characterize the quality of an electropherogram obtained with all types of instruments generating DNA profiles (RaphidHIT™ 200, DNA Scan™ Rapid DNA Analysis™ System, 3100 ABI Prism® Genetic Analyzer, MegaBACE sequencer, etc.);

it can be applied to any type of capillary electrophoresis with molecules of DNA (single or double strand), RNA, polypeptides, proteins, organic medicinal products, inorganic anions and cations or any molecules that can be separated on the basis of the difference in their charge/size ratio;

it can be used with any type of detector associated with capillary electrophoresis (UV-visible photometer, Refractometer, Fluorometric detector, Electrochemical detector, Conductometer, Light-scattering detector, Mass spectrometer);

it is compatible with different chemical conversions (addition of fluorochromes, etc.) required for the detection of molecules by the aforementioned detectors.

The proposed solution is easy to implement. First the size markers used therein are chemical products for which production is established and low-cost. Secondly, implementation thereof for a posteriori processing can be conducted by adding an operating function in the software available to persons skilled in the art. Finally, the implementation thereof in an automated process merely requires the addition in the machine programme of a processing algorithm to detect the double-peaks of the size marker.

According to a further aspect, there is proposed an electrophoresis method wherein a sample to be analysed is subjected to migration by electrophoresis during which at least one detector generate an electropherogram signal, characterized in that:

at least one sample subjected to migration by electrophoresis contains a size marker of the aforementioned type, and in that:

the electropherogram signal and/or data corresponding thereto are processed to detect the presence of the double-peaks corresponding to the pairs of molecules of said marker.

In particular, for a capillary electrophoresis method, it is verified for example whether the detection of the double-peaks corresponding to the pairs of molecules of said marker is or is not satisfactory, and a capillary is changed depending on the result of this verification or of prior verifications.

The processing of the electropherogram signal and/or of data corresponding thereto to detect the presence of the double-peaks corresponding to the pairs of molecules of said marker is performed in real-time or a posteriori.

The proposed solution is advantageously used for the detection of allelic variations between individuals as part of forensic analysis.

DESCRIPTION OF THE FIGURES

FIGS. 1a and 1b illustrate an example of an electropherogram profile (FIG. 1b) obtained with a size marker containing two pairs of molecules (FIG. 1a) adapted to generate double-peaks in an electropherogram.

FIGS. 3a1-3a3 and 3b1-3b3 illustrate an example of a set of loci and alleles it is sought to detect for forensic analysis.

FIGS. 5a and 5b first illustrate a theoretically expected electropherogram for a marker conforming to one possible embodiment, and secondly an electropherogram typically obtained.

FIG. 6 illustrates the superimposing of the quality curve of electropherogram resolution over an electropherogram (here that of the compound comprising the double-peaks). The quality curve, plotted using the values of Q, is obtained using the method of the invention.

FIG. 7 illustrates the method to detect double-peaks when considering value H relative to a threshold as described in the invention. V is the height of the valley to be considered for comparison with signal noise in order to estimate quality of resolution as described in the invention.

FIG. 8 illustrates the different situations in which a double-peak of the invention can be identified. The parameters A, B, V and the valley floor are explained therein. More specifically the double-peak M shows a valley floor above the noise level (the bases of the peaks of the double-peak merge on the valley). The electropherogram signal (function of the quantity of matter detected) indicates that the matter forming the two peaks is not separable in the region defined as valley of this double-peak and that the resolution decreases. The double-peak M+1 shows a valley floor at noise level. The signals of the peaks of the double-peak are therefore separable. The double-peak M+2 shows a valley floor below noise level. The signals of the peaks of the double-peak are largely separable. The double-peak M+3 shows a valley floor below noise level. Since the resolution of the electropherogram is greater than expected, the valley is wide which means that it is possible to distinguish noise between the two peaks. The valley floor is then the minimum read-out in the valley (for determination of V).

DETAILED DESCRIPTION OF ONE OR MORE POSSIBLE EMBODIMENTS AND IMPLEMENTATIONS

Marker Molecules

Figure 1:
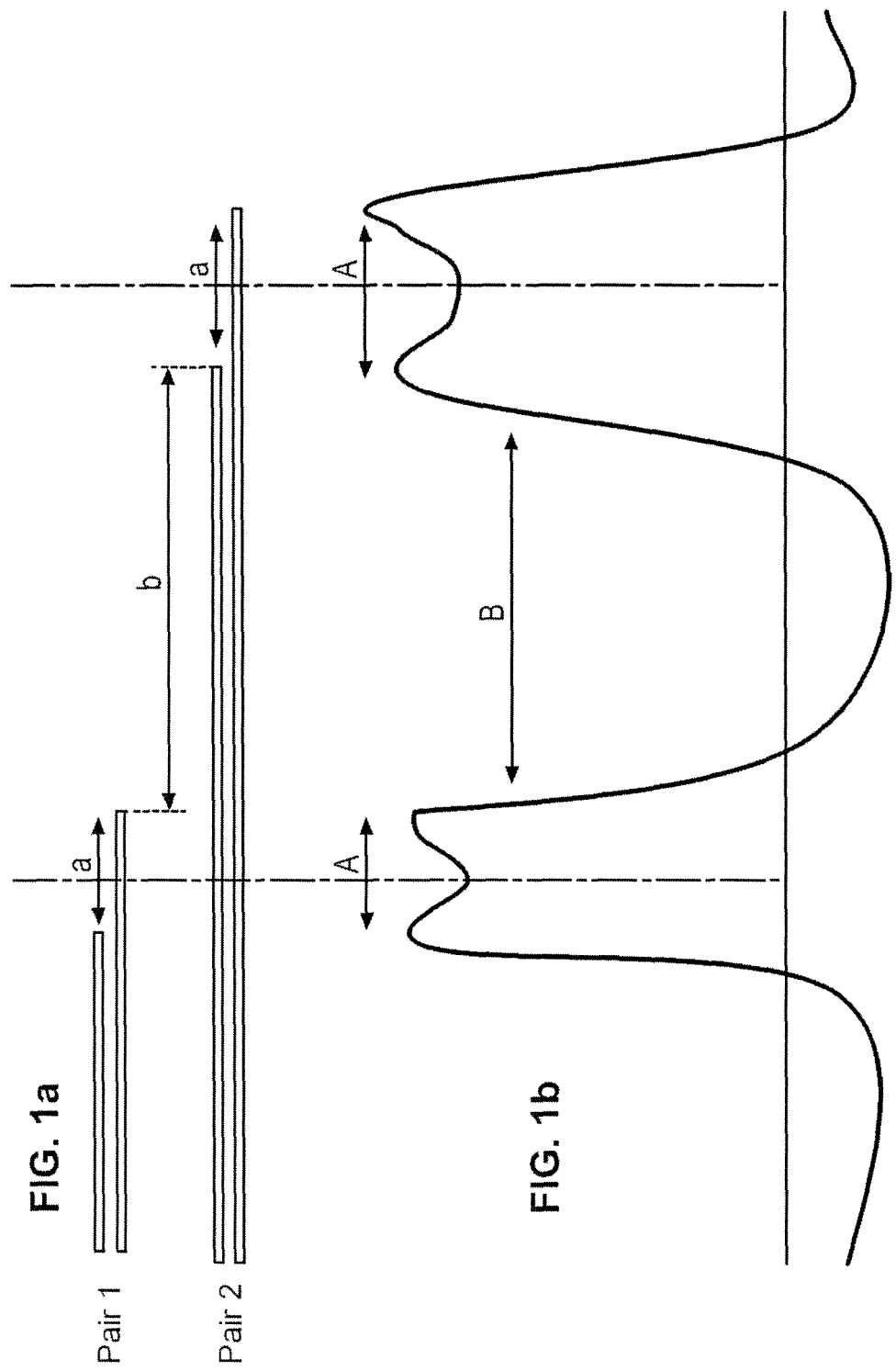

One example of a possible size marker is a marker containing five pairs of molecules of close size e.g. DNA molecules having the following sizes: [60, 61], [80, 81], [100, 101] and [120, 121] bp.

Other examples of sets of molecule pairs are evidently possible provided they are selected to allow to appear in an electropherogram successive double-peaks that are spaced apart by a distance greater than the distance between the two peaks generated by the molecules of one same pair, so that it is possible to detect the double-peaks.

In general, the number of double-peaks must be able to encompass the size values of the molecules to be separated during electrophoresis. The purpose is to obtain valid local resolution for the entire electropherogram.

The size marker may evidently contain a number of molecule pairs different from five. A number of molecule pairs between five and twenty is preferred however.

The molecules contained in a said size marker may be molecules of DNA (single or double strand), RNA, polypeptides, proteins, organic medicinal products, inorganic anions and cations. More generally, all molecules able to be separated on the basis of the difference in their charge/size ratio could be used. In one preferred embodiment, the molecules contained in this size marker are molecules of DNA (single or double strand), RNA molecules or polypeptides. In one particularly preferred embodiment, the molecules contained in said size marker are DNA molecules (single or double strand).

However, the molecules of the marker are selected as a function of the compounds it is sought to analyse in the electropherogram. In particular when the compounds that it is sought to analyse have an expected size in a certain region of the electropherogram, it is preferable to use a size marker containing molecules which will migrate in the same region and hence being of similar size.

The molecules of the marker are additionally selected so that they are of the same type as the molecules of the sample it is sought to analyse so that their corresponding peaks are effectively able to be used as benchmark to control resolution.

The size of the molecules to be analysed will not be the same depending on whether said molecules are polynucleotides, polypeptides, etc. For example the size of a polypeptide, which is a function of the number of its constituent amino acids, is generally expressed in kDa. The size of a polynucleotide, which is dependent on the number of its constituent base pairs, is expressed in base pairs (bp) for double strand DNA or in bases (b) for single strand DNA or RNA. When the pairs of molecules of the marker are of same type as the molecules of the sample it is sought to analyse, the double-peaks they generate allow verification that the electropherogram does indeed have the expected resolution in units of kDa, base pairs (bp), bases (b), etc. corresponding to the molecules of the sample.

Also, as indicated above, it is important that within each pair of molecules contained in said marker, said molecules should be of sufficiently close size to generate "double-peaks" in an electropherogram. In practice, this means that the size of the two molecules within each pair differs by at least one unit (one amino acid for polypeptides, one base pair for polynucleotides, one monomer for polymers, etc.), and that this difference is detectable in the electropherogram. It is to be noted that the smaller the size difference between the two molecules of each pair, the more it will be possible to guarantee reliable, accurate resolution of the electropherogram. On the other hand, too great a difference will not allow easy detection of "double-peaks".

In this entire text and as illustrated in FIGS. 1a and 1b, "a" designates the difference in size between two molecules of one same pair and "A" designates the distance between the apexes of the double-peak generated by said pair. "b" designates the size difference separating the pairs of molecules within the marker, it being understood that by "separation" is meant the difference in size between the longest molecule of a first pair and the shortest molecule of the following pair (cf. FIG. 1a). "B" designates the distance between the last peak of a first double-peak and the first peak of the following double-peak, separating the double-peaks generated in the electropherogram by two successive pairs of molecules (cf. FIG. 1a). As will have been understood, the values "A" and "B" are mean values, the sizes of the molecules contributing to the generation of one same peak possibly having some distribution between them.

On the Size Difference "a" Between the Molecules of One Same Pair

The size difference "a" of a pair generating a double-peak is dependent on the type of molecules contained in the marker. According to the type of these molecules it is expressed in base pair(s), kDa, number of monomers, etc. It is also dependent on the electrophoresis system used (type of electrophoresis, temperature and reaction time, gel used, etc.), since while it is desirable that this size difference "a" should be fairly small, it is nevertheless essential that despite this small difference in size the signals corresponding to the two molecules of each pair must be detectable in the electropherogram.

It is also selected as a function of the desired resolution and hence of the technical field and objective of the analysis performed.

Figure 2:
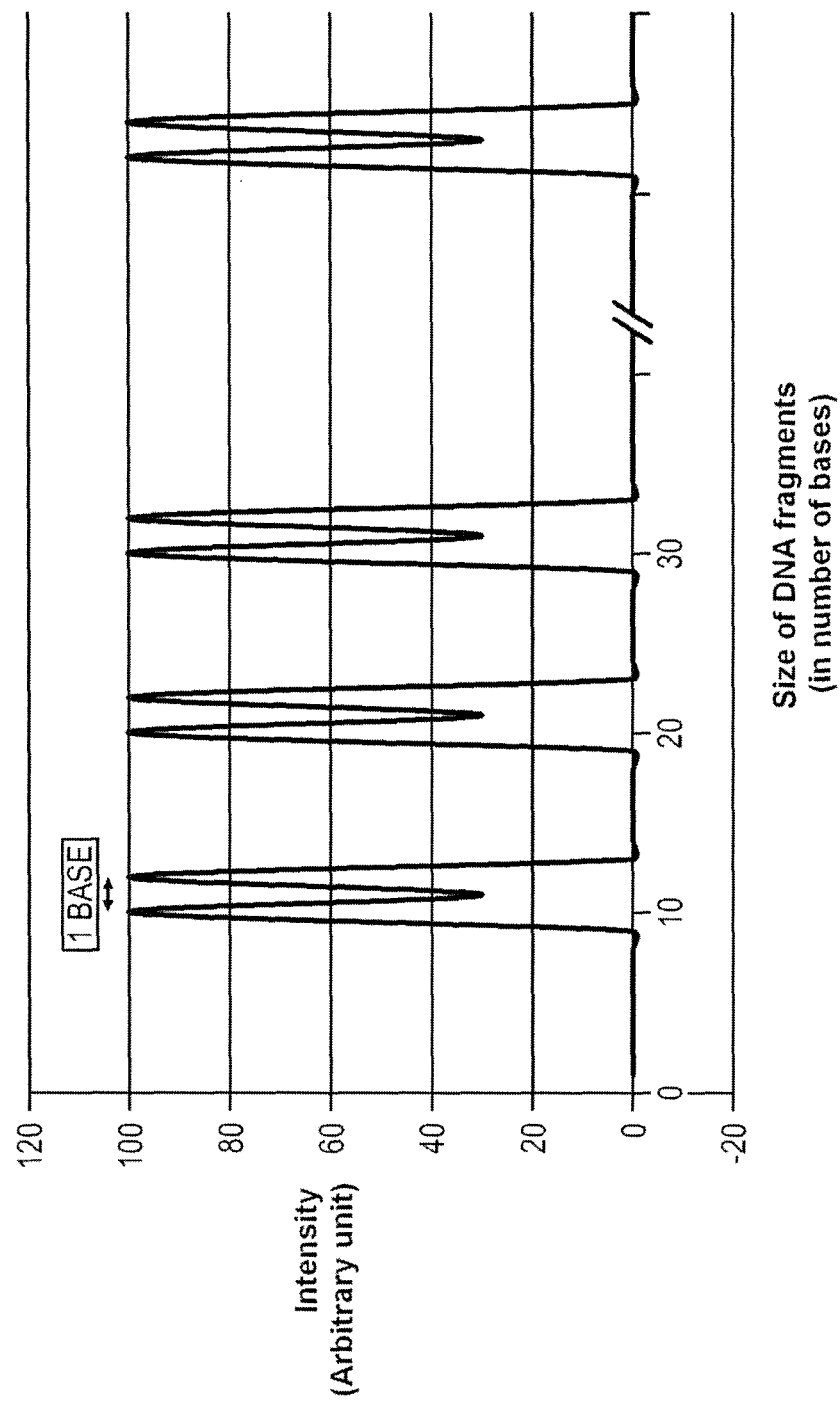
FIG. 2 illustrates an example of an electropherogram obtained with a marker of the invention when "a" equals 1 base and "b" equals 10 bases.
Figure 3A:
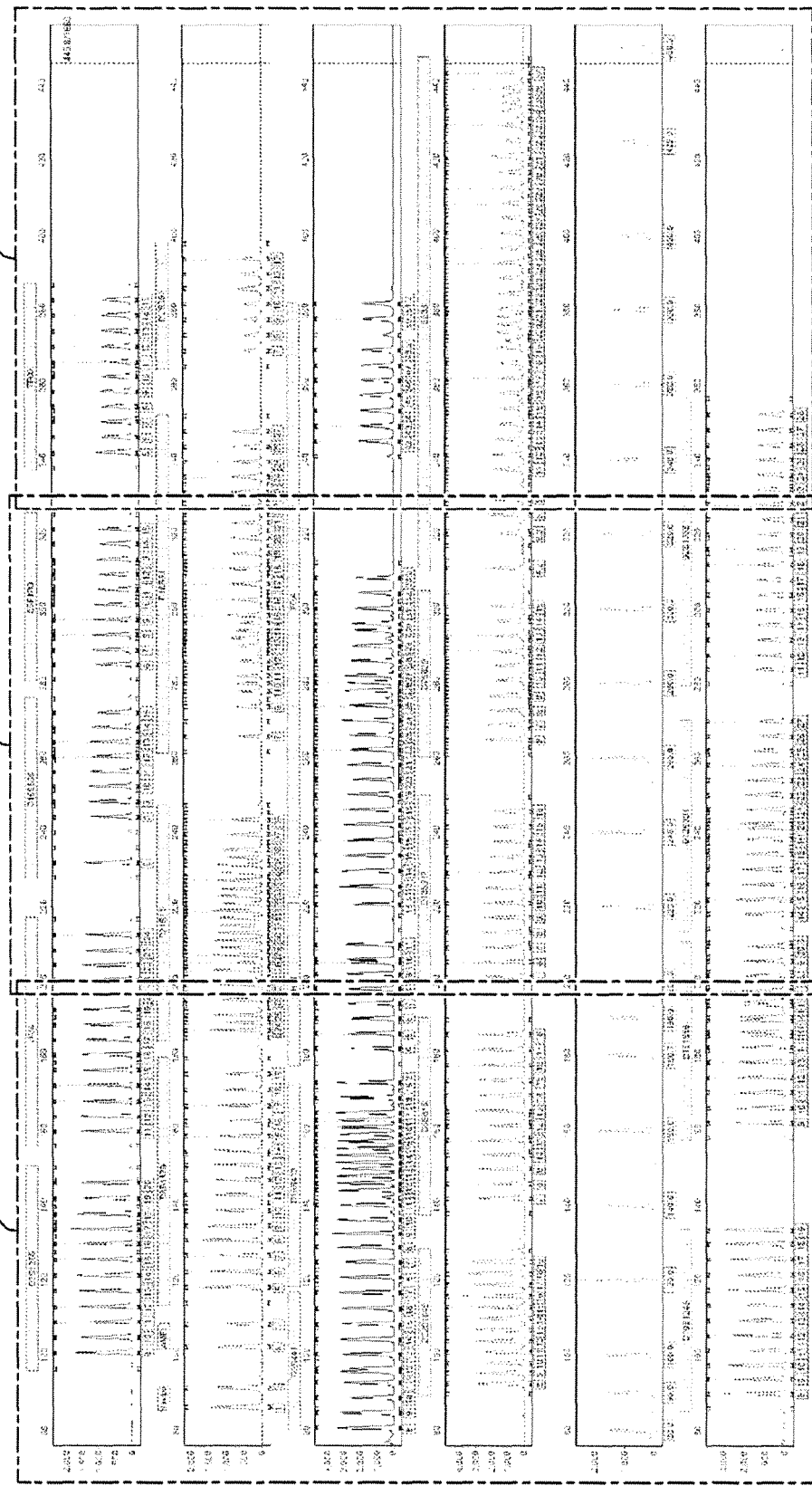
Figure 3B:
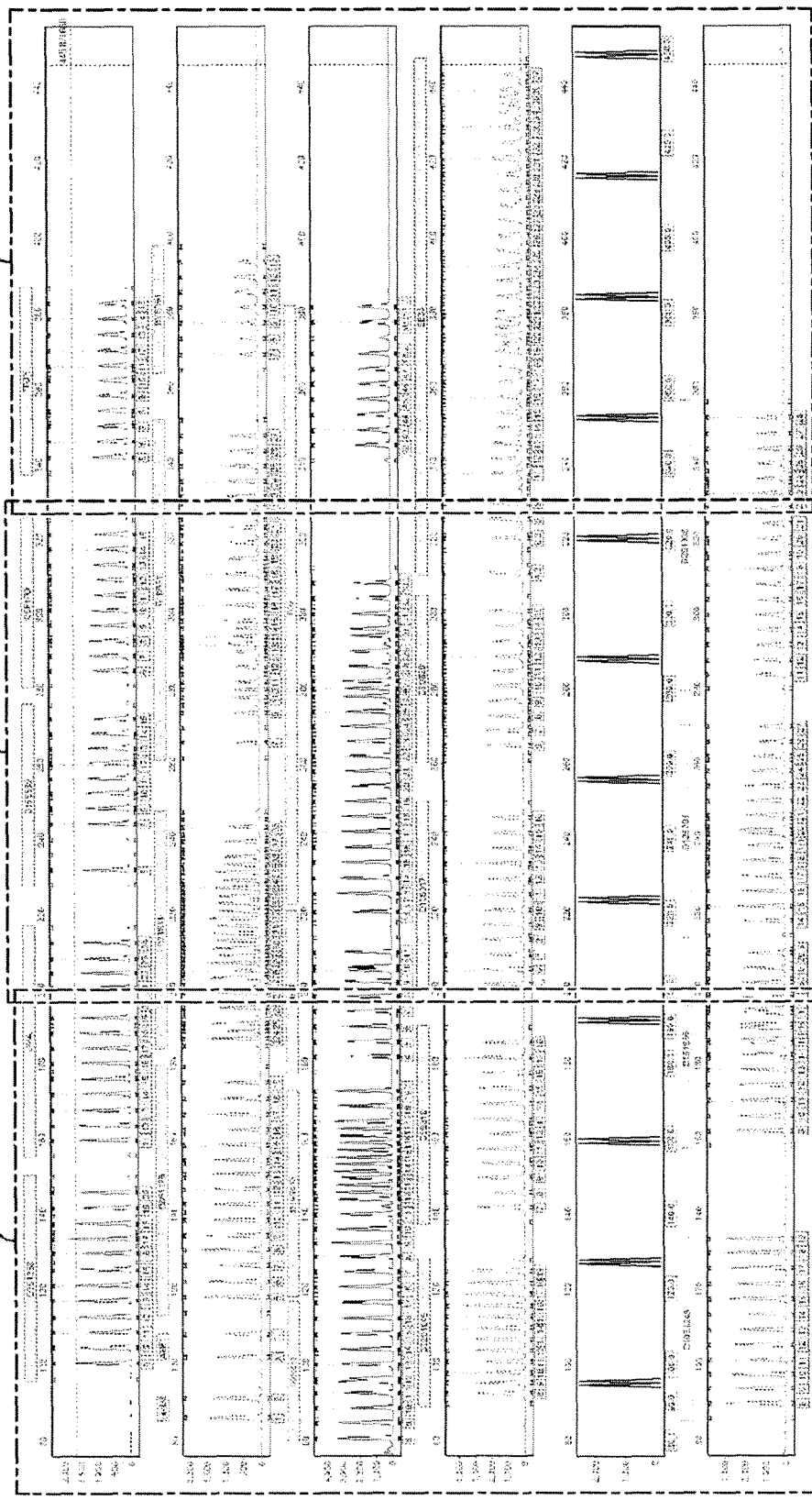

For example when analysing allelic variations between individuals (forensic analysis) it is preferable as illustrated in FIG. 2 to use pairs of molecules differing in size by only one base pair. The detection of a double-peak corresponding to two DNA molecules separated by only one base pair allows differentiation of alleles 9.3 and 10 of locus TH01 or any other microvariant, irrespective of its position in the profile (see FIGS. 3a1-3a3 and 3b1-3b3). Therefore in this particular technical field, the value of "a" is identical for each pair of molecules contained in the proposed marker. Preferably this value is constant and equals 1 bp.

However, for other applications not requiring this resolution (for example for the separation of two DNA sequences of very different size, or having molecules that are more difficult to separate in an electropherogram), it is possible to use pairs of molecules differing in size by more than one base pair (for example two, three even four base pairs).

It can also be envisaged, in some technical fields (for example to separate DNA sequences having sizes of 10, 50, 51 and 100 bp) to seek to obtain different resolution values in different regions of the electropherogram. In this case, it will be necessary to vary the interval "A" between the peaks of a double-peak using pairs of molecules for which the value of "a" is not identical.

In general, it is preferable however in order to ensure reliable calculation of resolution, that the difference in size between the two molecules of each pair ("a") does not exceed six units: for example "a" is comprised between 1 and 6 base pairs for a double-strand DNA sample, between 1 and 6 bases for a single-strand DNA or RNA sample, between 1 and 6 amino acids when the sample to be examined contains proteins or polypeptides, between 1 and 6 monomers when the sample to be examined contains polymers formed of a succession of monomers.

On the Size Difference "b" Between Pairs of Molecules

Another important parameter for the choice of marker molecules is the spatial distribution of the double-peaks of the marker molecules in the electropherogram.

When the compounds it is sought to analyse have an expected size in a certain region of the electropherogram, it is preferable to use a size marker containing molecules which will migrate in the same region (and hence being of similar size) and which will generate regularly spaced apart double-peaks in the electropherogram. This will allow accurate calculation of resolution in the region of the electropherogram in which the compounds will be identified. For example, if the sample to be analysed contains DNA fragments of about 100 bp, it is preferable to use a size marker in which the molecules have regularly distributed sizes between 50 and 150 bp so that it is possible to evaluate resolution over the entire region of interest (i.e. around the expected peaks).

In one particular embodiment, the value of "b" is identical between each pair of molecules contained in the marker (generating double-peaks regularly spaced apart along the electropherogram).

Alternatively, it is possible to vary the interval between each double-peak so as to increase or reduce the density of resolution data according to each region within one same electropherogram. The value of "b" will therefore be deliberately different between each pair of molecules of the marker so as to generate double-peaks spaced apart by a variable distance.

As explained above for parameter "a", the value of parameter "b" (and hence of the distance "B") is dependent on the experimental system used (type of electrophoresis, reaction conditions, etc.), and on the type and size of the compounds of interest to be analysed.

For example, when analysing allelic variations between individuals (forensic analysis) it is preferable to use pairs of molecules efficiently covering the entire electropherogram (i.e. about 600 bp) so that it is possible to provide resolution data throughout electrophoresis analysis. Also in this particular case, the mean sizes of these pairs of molecules must differ by no more than 60 bp so that the smallest loci have at least one resolution data item (i.e. a double-peak) in the width thereof. More specifically, having regard to the recommended loci for identification of individuals (see FIGS. 3$a$1-3$a$3 and 3$b$1-3$b$3 for an example) the ratio a:b which can be used for forensic analysis is 1:60 or higher, preferably 1:40 or higher and more preferably 1:35 or higher, these values of a and b remaining constant all through the electropherogram. In general when a kit is used, it is important that the distance "B" between double-peaks should allow resolution data to be obtained for the smallest loci in the region where the variants thereof are expected.

However, so that the method of the invention can be implemented, it is important that the "double-peaks" should effectively be identifiable in the electropherogram of the size marker of the invention. The latter must not therefore contain a series of single peaks which could be the case if distance A is similar to B. This is why distance B must be strictly greater than A. Preferably distance B is strictly greater than twice distance A. In other words, and since the distances A and B are proportional to the values of the parameters "a" and "b" respectively, it is preferable that the value of "b" should be strictly greater than twice the value of parameter "a" (b>2a).

For forensic analysis, it is not necessary to use pairs of molecules in which the size difference "b" is lower than 20 bp.

Therefore, for this particular application, the value of "b" is between 20 and 60 bp for example.

The molecules of the marker are preferably selected so that "b" equals 32 bp so that it is possible to calculate the resolution for analyses of the small loci D3S1358, D13S317 and TPOX.

The ratio a:b which can be used for forensic analysis is then 1:32, the values of 1 for "a" and of 32 for "b" remaining constant throughout the electropherogram.

For other applications, the distance between each double-peak ("B") may vary so as to be a function of the size variability of the molecules it is sought to identify by electrophoresis. As mentioned above, this distance is dependent on the type of sample to be analysed and on the size of the compounds of interest within this sample.

In addition, the molecules of the size marker are conjugated to a detectable marker so that the double-peaks can be caused to appear in the electropherogram so that it is possible to distinguish the molecules of the marker from the molecules contained in the sample to be analysed. The molecules of the marker may be conjugated to enzymes for example such as peroxidase, alkaline phosphatase, α-D-galactosidase, glucose oxidase, glucose amylase, carbonic anhydrase, acetyl-cholinesterase, lysozyme, malate dehydrogenase or glucose-6 phosphate dehydrogenase, or to a molecule such as biotin, digoxigenin or 5-bromo-deoxyuridine. Fluorochromes can also be conjugated to the molecules of the invention. These fluorochromes particularly include fluorescein and the derivatives thereof, rhodamine and the derivatives thereof, GFP (Green Fluorescent Protein), dansyl, umbelliferone, JOE, CXR-ET, Fluorescein, TMR-ET, CCS, 6-FAM™, VIC®, NED™, TAZ™, SID™, LIZ™ etc. Other conjugates may also include chemiluminescent markers such as luminol and dioxetanes, bioluminescent markers such as $^{123}$iodine, $^{125}$iodine, $^{126}$iodine, $^{133}$iodine, $^{77}$bromine, $^{99m}$technetium, $^{111}$indium, $^{113m}$indium, $^{67}$gallium, $^{68}$gallium, $^{95}$ruthenium, $^{97}$ruthenium, $^{103}$ruthenium, $^{105}$ruthenium, $^{107}$mercury, $^{203}$mercury, $^{99m}$rhenium, $^{101}$rhenium, $^{105}$rhenium, $^{47}$scandium, $^{121m}$tellurium, $^{122m}$tellurium, $^{125m}$tellurium, $^{165}$thulium, $^{167}$thulium, $^{168}$thulium, $^{18}$fluorine, $^{199}$yttrium, $^{131}$iodine.

Example of Application to the Field of Forensic Analysis

For the analysis of allelic variations between individuals, a size marker containing 28 pairs of molecules of single strand DNA of sizes (in number of bases) [60,61], [80,81], [100,101], [120, 121], [140,141], [160,161], etc. up to [600,601] was used.

It was therefore a size marker formed of molecules associated with other molecules the size of which contained an additional base (see FIG. 2).

The different loci and alleles of interest are shown in FIGS. 3$a$1-3$a$3 and 3$b$1-3$b$3.

Electrophoresis Method and Application of Control

It is possible to cause the above-described size marker to migrate independently of the sample to be analysed (for example in another capillary). In this case, the marker is essentially used to evaluate the size of the molecules contained in the sample to be analysed (and not the quality of analysis and/or of the capillary).

Figure 4A:
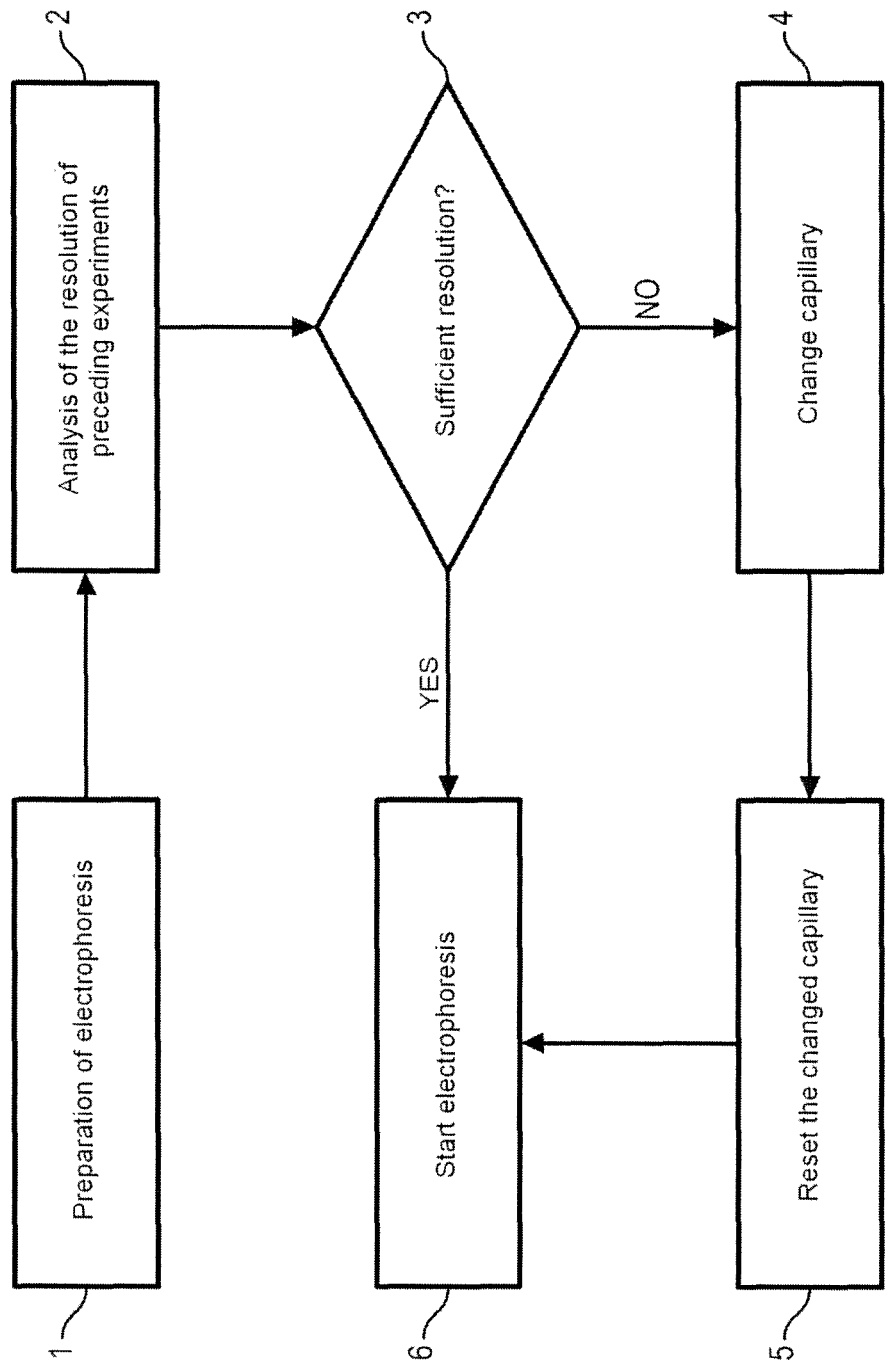
FIG. 4a gives a decision flow diagram of the quality of an electrophoresis capillary using the method of the invention.
Figure 4B:
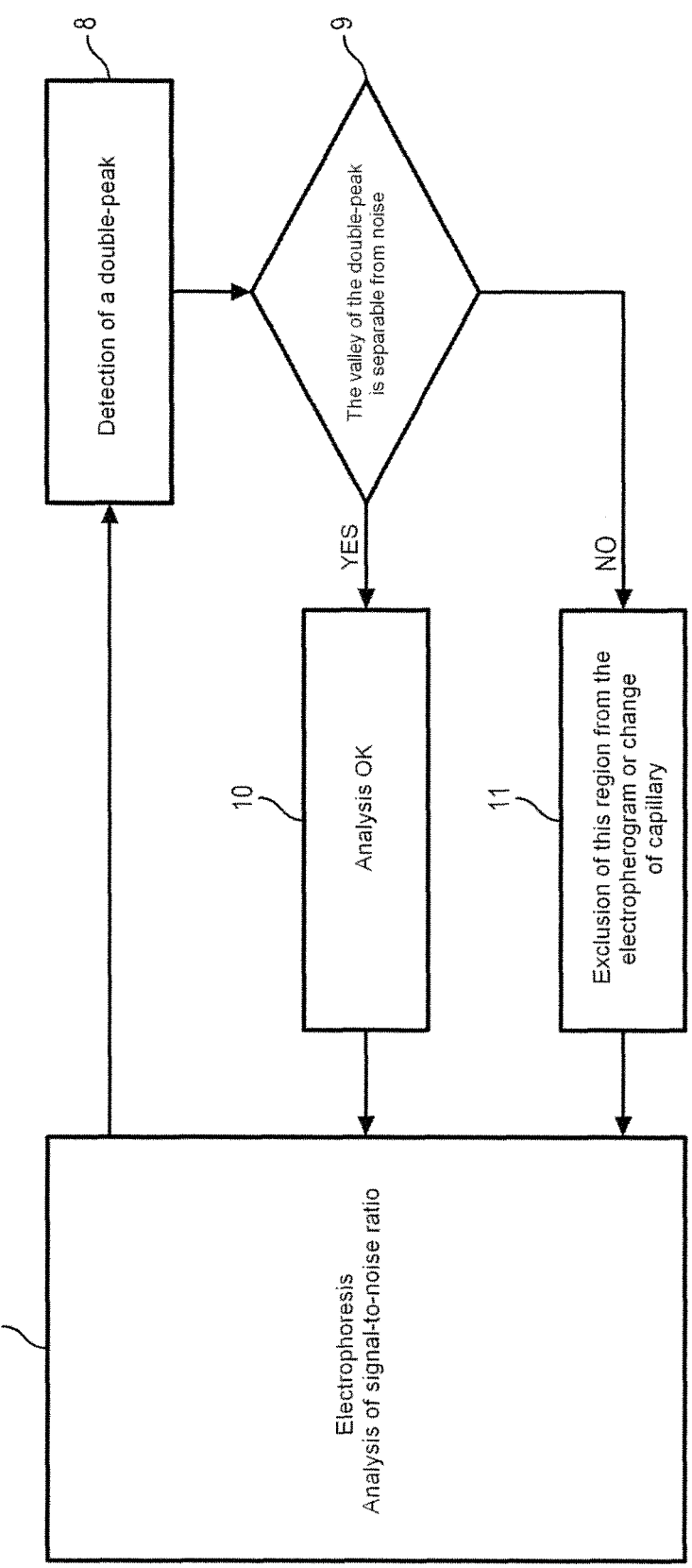
FIG. 4b gives a decision flow diagram of the quality of a double-peak in a given electropherogram.

However, in one preferred embodiment, said marker and sample to be analysed are caused to migrate concomitantly in one same capillary. In this case, prior to a new analysis with a given electrophoresis system, the size marker as described above is prepared and mixed with the sample to be analysed (step 1 in FIG. 4$a$).

When available, data on the resolution of previously conducted analyses are verified (step 2). If it is inferred from these data that the resolution is not satisfactory (test at step 3), the operator takes action on the electrophoresis system and for a capillary electrophoresis system for example changes the faulty capillary (step 4). After this change, the procedure for the capillary is reset and electrophoresis is set in operation.

Throughout the analysis by electrophoresis, the electropherogram signal of the marker (obtained by selecting the signals corresponding to the detectable marker carried by the molecules of said marker)—or numerical data corresponding to said marker—are analysed e.g. in real-time to control the resolution in the region of each compound of interest that is to be detected in the sample.

For this purpose, the signal-to-noise ratio is analysed on the electropherogram signal or on the data corresponding thereto (step 7 in FIG. 4$b$) and the presence is detected of the double-peaks corresponding to the pair of molecules of the marker (step 8).

To do so, it is verified that the two peaks corresponding to the separable molecules of the marker i.e. that the difference in height between the lowest of the two peaks and the hollow between the two peaks can be differentiated from noise (step 9).

One manner of proceeding is to quantitate, in the size marker electropherogram, the height of the valley separating the two peaks observed for the different pairs of molecules (value V in FIGS. 5a and 5b), and to compare this height with noise.

When a double-peak is detectable and when the valley of the double-peak is separable from noise, then the region containing this double-peak has resolution that is better than "a" (typically one base for forensic analysis). The analysis has satisfactory resolution (step 10) and can be continued by performing the different steps just described.

On the contrary i.e. if the valley of a double-peak cannot be separated from noise, the region under consideration does not have satisfactory resolution. In this case, the electropherogram is insufficiently resolved in this region. The analysis must be repeated e.g. with a new capillary. Failing this, the corresponding region in the electropherogram must be excluded for continuation thereof (step 11).

The calculation associated with resolution "a" is then conducted using statistical methods using standard deviation measurements, or the method developed by the inventors which is described in the example below. Other methods are described for example in Buel E. et al. (*J Forensic Sci.* 2001; 46(2):341-5).

The use of the above-described marker gives a reliable indication of the resolution of the electropherogram as and when analysis progresses. It is thus possible to measure accidental or time degradation of resolution to anticipate a maintenance operation (change of capillary, verification of experimental conditions, etc.) during analysis. It is also possible to store data on the resolutions obtained in preceding analyses so as to predict whether the quality of following electrophoreses will be sufficient (electrophoresis can be performed) or insufficient (the capillary must be changed for example).

Example of Processing for Detection of a Double-Peak and Control of Resolution

The electropherogram is processed to detect therein all the peaks having a height higher than a given peak detection threshold, and for all the peaks thus obtained it is determined which pairs formed of two successive peaks appear in the electropherogram with a separation lower than a given double-peak detection threshold.

One possible test to verify the presence of the double-peaks for all the pairs thus obtained is to verify that the difference in height V between the smallest peak of a double-peak and the valley of this double-peak is equal to or higher than 3 times the value of the standard deviation r of the height of the valleys measured from the preceding double-peak to the following double-peak.

If a size marker is considered containing at least three pairs of molecules generating three double-peaks (denoted $M_{-1}$, M and $M_{+1}$ in FIGS. 5a and 5b) the test performed on an electropherogram may be as follows:

1) For the double-peak denoted M, calculation of the standard deviation r of the height of the valleys from double-peak $M_{-1}$ to double-peak $M_{+1}$, this standard deviation being $$\sigma = \sqrt{\frac{\Sigma(x-\bar{x})^2}{n}},$$

where x=measurement of valley height, $\bar{x}$=mean of valley height measurements and n=the number of valleys.

The height of a valley x is calculated over three significant measurements (X, Y, Z) where Y is lower than X and Z. The value x is equal to the lowest of the two results from among X−Y or Z−X.

2) Measurement of the height difference between the smallest peak of the double-peak M and the valley floor for this double-peak M, this difference being denoted V.

In the local portion under consideration, the distribution of valley heights follows a normal or equivalent law implying that, if $V \geq 3\sigma$, then the probability that the valley separating the peaks of the double-peak is the sought-after valley is 99.73%. The same probability of double-peak detection is associated therewith, this valley characterizing a double-peak.

3) Comparison of value V with $3\sigma$ (three times the value of r calculated above).

Since the sought-after valley separates two characteristic peaks of molecules differing by "a" bases, if $V \geq 3\sigma$ then the two peaks of the double-peak are separable to within "a" base(s), implying a resolution better than "a".

The analysis is then reliable.

It is further possible to measure the reliability of the upper limit of resolution in relation to "a" by calculating the following value Q on each peak:

$$Q = \frac{V}{3\sigma}.$$

If V is insufficient to detect the valley of the double-peak (and hence the double-peak) then Q<1.

As a result, if the resolution in a region of a double-peak with Q<1 is greater than "a", this region must not be taken into consideration.

In this manner, each double-peak M is associated with a value Q.

Via interpolation of Q values (linear regression, curvilinear fit . . . ), a reliability curve is obtained (FIG. 6) which allows detection of the regions in the electropherogram which have resolution higher than "a" and must not be used (regions in which the Q curve passes below 1 and where the reliability of resolution is insufficient).

This curve can also be used to assess the condition of a capillary over time by superimposing the Q curves obtained over each electropherogram e.g. at the time of screen display.

Other Processing Examples

For all electropherogram analyses, calculation of the detection limit is performed to separate noise from the signal (cf. FIG. 5b).

For example, for DNA fragments, this detection limit is measured for each electropherogram instrument and each PCR kit. It is measured for the fluorochrome marker of the double-peaks.

The detection limit is chosen to be well above noise and is equal for example to the standard deviation of noise multiplied by a coefficient routinely ranging from 3 to 10. Only the peaks above this detection limit are analysed and sorted (alleles or artefacts).

For a double-peak generated by molecules separated by one base pair, several methods can be used to detect separation.

To detect the presence of a double-peak, different methods can then be used:

1) Calculation of signal derivatives to detect slope changes of the signal: for a signal of good quality, after the maximum value of the 1st peak, the slope becomes negative then passes through zero before re-becoming positive to reach the 2nd maximum corresponding to the 2nd peak.

2) Calculation of the height of the valley (FIG. 7) between the two peaks (value V) and of the height of the smaller of the two peaks (H). The ratio is then calculated between Q=valley height (V)/height of the smaller of the two peaks (H). Q=V/H.

The minimum threshold of this ratio Q can be adjusted in relation to the starting quality of the electropherogram instrument.

The ratio Q can be plotted over time to measure potential degradation of resolution.

If this ratio Q falls below a critical adjustable threshold (typically a minimum threshold of 10) an alert must be given to indicate loss of resolution and to request maintenance of the instrument.

The different processing operations just described are for example carried out numerically or they are performed on a computer. The processing programme can be downloaded for example onto a microprocessor/computer of the electrophoresis machine for the conducting of real-time analysis. Analysis can also be performed a posteriori, for example at the time of subsequent controlling of the results of a forensic analysis.

The invention claimed is:

1. A size marker for electrophoresis, characterized in that it contains several pairs of molecules the sizes of which are selected to allow the generation of a succession of only double-peaks in one same electropherogram, said double-peaks being spaced apart two by two by a distance greater than the distance separating the two peaks of a doublepeak, and characterized in that the size difference ("b") between pairs of molecules contained in said marker and which correspond to successive double-peaks is greater than twice the size difference ("a") between two molecules of one same pair (b>2a).

2. The marker according to claim 1, wherein said molecules are molecules of DNA or RNA, and characterized in that the size difference ("a") between two molecules of one same pair is between 1 and 6 base pairs.

3. The marker according to claim 2, wherein "a" equals 1 base pair.

4. The marker according to claim 1, wherein said molecules are molecules of DNA or RNA, and characterized in that "b" is equal to between 20 and 60 base pairs.

5. The marker according to claim 4, wherein "b" equals 32 base pairs.

6. The marker according to claim 1, characterized in that it contains at least three pairs of molecules, each adapted to generate double-peaks in one same electropherogram.

7. The marker according to claim 1, wherein said molecules are chosen among: single or double strand DNA, RNA, polypeptides, proteins, organic medicinal products, inorganic anions and cations.

8. The marker according to claim 1, characterized in that it comprises pairs of molecules which generate double-peaks in different regions of the electropherogram which correspond to different size differences "a".

9. The marker according to claim 1, characterized in that it comprises pairs of molecules which generate double-peaks in different regions of the electropherogram which correspond to constant size differences "a".

10. The marker according to claim 1, characterized in that the size difference ("b") between the pairs of molecules generating successive double-peaks is identical for the whole marker, the double-peaks being regularly spaced along the electropherogram.

11. The marker according to claim 1, characterized in that the size difference ("b") between pairs of molecules generating successive double-peaks is variable.

12. A method for controlling the resolution of an electropherogram, characterized in that a signal corresponding to said electropherogram and/or data corresponding thereto are processed to detect the presence of double-peaks corresponding to the pairs of molecules of a marker according to claim 1.

13. The method according to claim 12 wherein, to detect the presence of a double-peak, the ratio between the following is compared with a threshold:
the difference in height between the smallest peak of a double-peak and the valley of this double-peak; and
three times the value of the standard deviation ($\sigma$) of the height of all the valleys of the baseline signal from the preceding double-peak to the following double-peak.

14. The method according to claim 13, characterized in that the curve of this ratio is superimposed over a corresponding electropherogram.

15. The method according to claim 12, wherein, to detect the presence of a double-peak, the slope changes of the electropherogram signal are detected and it is detected that its slope becomes negative after a first maximum, passes through zero and re-becomes positive to reach a second maximum.

16. The method according to claim 12, wherein, to detect the presence of a double-peak, comparative processing is performed whereby the ratio between the height of the valley between two peaks and the height of the smallest of the two peaks is compared with a threshold.

17. A computer programme product adapted to implement the steps of the method according to claim 12 when it is run on a computer.

18. An electrophoresis method wherein a sample to be analysed is subjected to migration by electrophoresis during which at least one detector generates an electropherogram signal, characterized in that:
at least one sample subjected to migration by electrophoresis contains a size marker according to claim 1, and in that
the electropherogram signal and/or data corresponding thereto are processed to detect the presence of doublepeaks corresponding to the pairs of molecules of said marker.

19. The capillary electrophoresis method according to claim 18, characterized in that it is verified whether the detection of the double-peaks corresponding to the pairs of molecules of said marker is or is not satisfactory, and a capillary is changed as a function of the result of this verification or of prior verifications.

20. The electrophoresis method according to claim 18, characterized in that the processing of the electropherogram signal and/or of data corresponding thereto to detect the presence of the double-peaks corresponding to the pairs of molecules of said marker is performed in real-time or a posteriori.

21. The electrophoresis method according to claim 18, characterized in that it is performed to detect allelic variations between individuals as part of forensic analysis.

* * * * *